United States Patent
Sprogar et al.

(10) Patent No.: US 7,150,784 B2
(45) Date of Patent: Dec. 19, 2006

(54) PIGMENT-CONTAINING GEL MASS VASED ON LIPIDS

(75) Inventors: Christian Sprogar, Bubenreuth (DE); Reinhard Pinzer, Schnaittach (DE)

(73) Assignee: Schwan-Stabilo Cosmetics GmbH & Co. KG, Heroldsberg (DE)

( * ) Notice: Subject to any disclaimer, the term of this patent is extended or adjusted under 35 U.S.C. 154(b) by 171 days.

(21) Appl. No.: 10/500,527

(22) PCT Filed: Jan. 14, 2003

(86) PCT No.: PCT/EP03/00300

§ 371 (c)(1),
(2), (4) Date: Feb. 11, 2005

(87) PCT Pub. No.: WO03/060024

PCT Pub. Date: Jul. 24, 2003

(65) Prior Publication Data

US 2005/0211132 A1    Sep. 29, 2005

(30) Foreign Application Priority Data

Jan. 16, 2002 (DE) ................................ 102 01 370

(51) Int. Cl.
*C09D 11/00* (2006.01)
(52) U.S. Cl. .................................. 106/31.6; 106/31.69

(58) Field of Classification Search ............... 106/31.6, 106/31.69
See application file for complete search history.

(56) References Cited

U.S. PATENT DOCUMENTS

| | | | |
|---|---|---|---|
| 2003/0113356 A1* | 6/2003 | Deckner et al. | ............. 424/401 |
| 2004/0234458 A1* | 11/2004 | Riedel et al. | ................. 424/47 |
| 2005/0004274 A1* | 1/2005 | Healy et al. | ................... 524/80 |

\* cited by examiner

*Primary Examiner*—J. A. Lorengo
*Assistant Examiner*—Veronica Faison-Gee
(74) *Attorney, Agent, or Firm*—Bachman & LaPointe, P.C.

(57) ABSTRACT

A pigment-bearing gel material based on lipids and color pencils containing same, which is characterized in that it has a combination of oil-soluble alkylcellulose whose alkyl residues can be straight-chain or branched and preferably have have between 1 and 10 carbon atoms, an alkylgalactomannan polysaccharide whose alkyl residue preferably has between 1 and 10 carbon atoms and a salt which was obtained from a long-chain fatty acid with preferably between 16 and 24 carbon atoms and a fatty acid amidoalkyldialkylamine of a fatty acid with between 16 and 24 carbon atoms and processes for the production of same.

32 Claims, No Drawings

PIGMENT-CONTAINING GEL MASS VASED ON LIPIDS

The invention concerns pigment-bearing gel materials based on lipids, color pencils containing same and processes for the production of pigment-bearing gel materials and color pencils containing such gel materials.

Pigment-bearing gel materials based on lipids are disperse systems which comprise a network of the gel-forming component with lipid incorporated therein. The gel material also contains pigments for coloring purposes and possibly also fillers which are insoluble therein. Materials of that kind are suitable for the application of colors in many sectors. The main areas of use that can be considered for pigmented gel materials are coloring materials for drawing and painting and for the area of decorative cosmetics where they can be used in many forms, inter alia in the form of creamy makeup or in the form of a makeup pencil, creamy eyeshadow or in the form of an eyeshadow pencil, in the form of rouge, lipstick, eyeliner pencil and also eyebrow pencil and in the form of a kohl or kajal pencil. In particular such pigment-bearing gel materials based on lipids can be used for the production of cosmetic pencils.

Materials used for drawing, painting and for makeup should be such that they can be easily applied but, after having been applied, they should have good durability and should be as water-proof as possible, and in the case of cosmetic pencils should also be tear-proof as well as transfer-resistant, that is to say they should not come off on to other articles such as for example glasses or textiles and they should not migrate or bleed out of the region in which they are applied.

Known color pencil compositions are based on a blend of fats, oils and waxes, which is colored with pigments. Thus the standard works which are known to the appropriately involved man skilled in the art describe for example lipsticks or eyeshadow pencils comprising pencil formulations made up from natural or synthetic triglycerides, hardened oils, cocoa butter, coconut oil, natural or synthetic oils or paraffin oils, silicone oils, natural or mineral waxes and usual additives such as lanolin or lanolin derivatives. Those preparations may possibly also contain known cosmetic 'active substances', for example based on oil-soluble plant extracts, bisabolol or vitamins. In general those preparations represent thixotropic systems which liquefy under the shearing forces occurring upon application and thus permit soft gentle application.

It is also known for example to employ such preparations, using volatile substances such as for example short-chain linear or cyclic silicone oils, known to the man skilled in the art as dimethicone or cyclomethicone, or volatile hydrocarbons, in particular isoparaffins, or mixtures thereof. Such preparations can be particularly softly and gently applied and, after evaporation of the volatile constituents, what remains behind is a flexible lipid film with transfer-resistant properties, which also exhibits only slight tendencies to migrate into the fine creases and folds in the skin.

Such gel-like preparations have hitherto been used in the cosmetics sector predominantly for deodorant and antiperspirant sticks. In general terms those gels have the advantage that they can be easily applied but at the same time they suffer from the disadvantage that they cannot be mechanically loaded. In that respect the advantage of easy applicability predominates in regard to deodorant sticks, and no major significance is attributed to stability, by virtue of the form of those sticks.

In relation to their length deodorant sticks are of a relatively large diameter and the requirements in terms of strength are not very high by virtue of the structure of the sticks. It was found that materials which are well suited for deodorant sticks can only be limitedly shaped to form thinner sticks and leads and, in particular as the materials are too soft, they can only be removed from the mold with great difficulty or not at all. In particular leads for cosmetic pencils are generally of diameters in the range of between 2 and 10 mm.

The attempt has therefore been made to produce such oleogels using waxes for example beeswax, candelilla wax or carnauba wax and shape them to form leads. Beeswax shrinks upon being cooled and is therefore suitable for materials which are to be processed by heating above their softening point and molding in suitable molds and cooling to form stick blanks. Candelilla wax and carnauba wax give the oleogels shine and are therefore popular with lipsticks and eyeshadow pencils. It was found however that the known oleogels have an excessively low oil binding capability so that ageing in the case of prolonged storage and when changes in temperature occur can result in syneresis effects, which results in oil separation phenomena, so-called 'sweating', which can go as far as complete phase separation phenomena. The oil contained in the material initially issues in the form of droplets and later moves into the surrounding area, which adversely affects the esthetic appearance of the pencil. In addition due to the discharge of oils the pencils lose their elasticity and become brittle. It was further found that the leads produced from the material shrink so severely due to the oil diffusing away, evaporating or migrating, that, in an attempt to produce color pencils, leads inserted in wood slip out of the wood sheaths after a short time. If lead materials of that kind for producing color pencils are cast in plastic sheaths or in rotary mechanisms of plastic material, it was found that oil migrating out of the lead spreads along the inner and outer walls and adversely affects the function even of those color pencils. It was further found that very thin leads of diameters in the range of around between 2 and 4 mm have excessively low resistance to fracture, which, upon being removed from—preferably metallic—casting molds results in considerable breakage and thus reject wastage. If casting is effected directly into rotary mechanisms using modern processes, then in the event of a lead breakage the entire rotary mechanism generally has to be discarded as waste.

Therefore an object of the invention was to eliminate the disadvantages hitherto connected with color leads and so improve known pencil materials that color leads with a soft delivery and a high proportion of oil can be processed in accordance with the usual technologies—such as extruding a material to form elongate extrusions and introducing extrusion portions which have been cut to length into wood or other suitable materials in accordance with the processes known in the production of lead pencils, pouring a material which is heated above the melting point into preferably metallic casting molds and inserting castings obtained after cooling into suitable application members, pouring a material which has been heated above the melting point into a casing of an injectable material or pouring such a material into the lead guide part of a rotary mechanism. In particular the invention seeks to provide that it is possible using those known processes to produce thin colored leads of diameters in the range of between 2 and 4 mm, which have sufficient tensile strength, flexural strength and resistance to fracture.

A further object of the invention was to produce such color pencils in such a way that, with a high proportion of oil and a soft delivery, which is desired in particular in relation to cosmetic color leads, they exhibit no tendency for oil to come out of same and thus they retain an esthetic appearance even after prolonged storage under fluctuating temperature conditions.

DE-OS No 199 10 870 describes a pigment-bearing oil-based gel material which contains a hydroxy fatty acid in combination with an alkylmethicone. Preparations of that kind are admittedly distinguished by a good oil binding capacity, but the flexural strength and resistance to fracture of thin leads for color pencils is certainly still capable of improvement. In addition EP-A 0 861 657 describes cosmetic materials whose film-forming properties and adhesion properties are said to be improved by the addition of ethylcellulose. In particular gel-like materials are said to be produced. DE-OS No 199 11 748 describes lead pencils which contain hydroxyalkylcellulose or alkylcellulose soluble in organic solvents. That addition is said to improve the tensile strength, flexural strength and resistance to fracture of color leads, in particular color leads of thin diameter and—measured thereagainst—great length. Oil-soluble alkylcellulose, in particular ethylcellulose, is however only poorly soluble in the waxes and oils known for the manufacture of color leads; in addition the amount used in materials which are heated above the melting point and which are to be processed in that condition by casting is greatly limited as they result in a severe rise in viscosity. The material easily becomes too viscous to be capable of being successfully poured into any openings of small diameter—more specifically in the range of diameters of the desired color leads (between 2 and 4 mm). The casting method known from DE-OS No 40 05 894, using movable filling needles, also only goes limitedly further, in relation to such highly viscous materials.

The extrusion of materials containing oil-soluble ethylcellulose is in principle possible but it requires extraordinarily high extrusion pressures. Therefore those publications do not attain the objects of the present invention.

Surprisingly it was now found that a combination of oil-soluble alkylcellulose whose alkyl residues can be straight-chain or branched and preferably have between 1 and 10 carbon atoms, with an alkylgalactomannan polysaccharide whose alkyl residue preferably has between 1 and 10 carbon atoms and a salt which was obtained from a long-chain fatty acid with preferably between 16 and 24 carbon atoms and a fatty acid amidoalkyldialkylamine of a fatty acid with between 16 and 24 carbon atoms, results in color leads with completely surprising stability properties. The latter may involve for example stearoylamidopropyl dimethylamine stearate or behenamidopropyl dimethylamine stearate or stearoylamidopropyl dimethylamine behenate or behenamidopropyl dimethylamine behenate or mixtures thereof. Quite particularly preferred in that respect is oil-soluble ethylcellulose in combination with a C1–5 alkylgalactomannan and behenamidopropyl dimethylamine behenate. The specified product designations involve the so-called 'INCI names' which are known to the man skilled in the relevant art.

C1–5 alkylgalactommanan and behenamidopropyl dimethylamine behenate are certainly known to the man skilled in the art as film-forming agents and as viscosity-increasing raw materials for non-aqueous systems. It was therefore all the more surprising to find that the specified combination of those two raw materials with oil-soluble ethylcellulose involved a markedly reduced level of viscosity of a pigmented mixture of fats, waxes and oils, heated above the melting point thereof, which resulted in a highly fluid, pourable material. In addition it was possible in that mixture—evidently by virtue of certain surface-active effects of the behenamidopropyl dimethylamine behenate—to dissolve somewhat larger amounts of oil-soluble ethylcellulose in that material, without in that respect involving the depositions of ethylcellulose, observed without that addition, or increases in viscosity. The combination of the three raw materials specified therefore resulted in a very homogeneous mixture with good pigment distribution and after pouring and cooling of the castings, that gave color leads which can be uniformly applied and which are pleasant to apply, in particular when such color leads are to be applied to the tender skin of the face in the region of the lips and eyes.

In that respect, the alkylcellulose, preferably an oil-soluble ethylcellulose, is used in a proportion of between 0.1 and 20% by weight, preferably between 0.25 and 10% by weight, quite particularly preferably between 0.3 and 6% by weight. The alkylgalactomannan, preferably the C1–5 alkylgalactomannan, is used in proportions of between 0.1 and 20% by weight, preferably between 0.25 and 10% by weight, quite particularly preferably between 0.4 and 4% by weight.

The salt which comprises a long-chain fatty acid with preferably between 16 and 24 carbon atoms and a fatty acid amidoalkyldialkylamine of a fatty acid with between 16 and 24 carbon atoms, preferably behanamidopropyl dimethylamine behenate, is used in proportions of between 0.1 and 30% by weight, preferably between 0.3 and 20% by weight, particularly preferably between 0.5 and 6% by weight. In that respect care is to be taken to ensure that the proportions of alkylcellulose, preferably oil-soluble ethylcellulose and alkylgalactomannan polysaccharide, preferably C1–5 alkylgalactomannan, are used in a ratio of between 0.3:1 and 3:1 relative to each other and the ratio of the salt which comprises a long-chain fatty acid with preferably between 16 and 24 carbon atoms and a fatty acid amidoalkyldialkylamine of a fatty acid with between 16 and 24 carbon atoms, preferably behanamidopropyl dimethylamine behenate is in a ratio of between 0.5:1 and 5:1 to the total amount of the other two constituents of the combination.

It was further surprising that the combination of the three specified raw materials, in the cooled condition, produces very attractive and homogeneous gel structures in which very large amounts of an oil component remain stably bound, so that separation or oil deposit phenomena do not occur even after a prolonged period of time—not even if the said color leads are stored under severely fluctuating temperatures.

That oil component which constitutes an essential constituent of the gel material according to the invention can include vegetable, animal, mineral or synthetic oil and/or fat and wax. Thus inter alia oils, fatty oils, fats, paraffins and petroleum jelly (Vaseline) are suitable for the present invention. The following may be named here by way of example: vegetable oils such as for example castor oil, sunflower oil, sesame seed oil, rapeseed oil, hydrated vegetable oils such as coconut oil or palm oil, jojoba oil, (INCI: Buxus Chinesis)—in the chemical sense a liquid wax—lanolin and lanolin derivatives, mineral oil, volatile isoparaffins, volatile and non-volatile silicone oils such as for example cyclomethicone, dimethicone, phenyltrimethicone and mixtures thereof. The oil is used in a proportion of between 1 and 70% by weight. Below 1% the material is too viscous even at temperatures markedly above the melting point, while above 70% by weight the gel structure is only inadequately formed and the finished color lead does not enjoy the desired good properties of use. The desired viscosity of the material can be suitably set by virtue of the choice of the nature and amount of the oil component, by means of a few routine tests. A part of the oil component can also be formed by wax. In this respect it is possible to use vegetable, animal, mineral and also synthetic waxes such as for example silicone waxes. The oil component used is preferably mixtures of oil-like and wax-like raw materials. If the gel material is to be used for color leads for cosmetic pencils, preferably a wax which is usual in cosmetics is employed, such as for example beeswax, carnauba wax, candlilila wax, Japan wax, ouricuri wax, flower waxes or fruit waxes such as orange flower wax, jasmine wax, apple wax or orange wax, lignite wax, microcrystalline wax, modified beeswax such as 'Cera Bellina', long-chain fatty alcohols such as cetyl alcohol, stearyl alcohol, isostearyl alcohol, behenyl alcohol, esters of long-chain fatty alcohols with long-chain fatty acids such as cetylpalmitate, cetearylpalmitate, stearylstearate, behenylstearate, C20–40 alkylstearate or mixtures of those waxes. In that respect beeswax gives a somewhat more matt application, while carnauba wax and candellila wax give a more strongly shiny application. Preferably volatile and/or non-volatile oils are used in the oil component. Particularly preferred in that respect are mixtures of volatile silicone oils such as cyclomethicone and/or short-chain dimethicone, possibly also mixed with volatile isoparaffins such as isoundecane and/or isododecane with waxes, fats, paraffins or fatty oils. In that connection the volatile constituents make it easier to apply the gel material to the skin, in particular that of the face, while on the other hand they enhance the durability and water-resistance or tears-resistance of the applied layer to a marked extent when the volatile components have evaporated off. With a suitable combination of the volatile components with the remaining oil component it is also possible to avoid what is known as the 'wind-burn effect'.

The proportion of wax is selected in dependence on the viscosity of the gel material heated above the melting point and the subsequently desired properties of the finished color lead. Preferably the proportion of wax in the overall composition is between 0.1 and 30% by weight.

The further constituent of the gel material, which is essential to the invention, is a pigment or a mixture of pigments. Here the substances which are usually employed for pigmented materials are used. For cosmetic materials, these are regulated in Germany by Appendix 3 of the Cosmetic Regulations which are based on the corresponding EC Directive. Comparative regulations also apply in Germany and the USA. Examples of suitable pigments are inorganic pigments such as titanium dioxide, iron oxides, ultramarine blue, chromium oxide green, chromium hydroxide green, Berlin Blue (Ferric Blue), mica, micas coated with titanium oxide and/or other metal oxides, lakes of organic coloring agents or mixtures thereof. In addition it is also possible to use finely divided, flake-form metal powder such as aluminum, brass, bronze, silver or gold or also finely divided PET flakes which exhibit interference phenomena. Preferably the pigments which are suitable for decorative cosmetics are used. The content of the pigment or the pigment mixtures in the gel material according to the invention is in a range of between 0.1 and 50% by weight, preferably between 1 and 40% by weight, depending on the color intensity of the pigment used and the subsequently selected technology for production of the finished color leads. An amount of between 5 and 30% by weight is quite particularly preferred.

In addition to the listed components the gel material according to the invention may contain still other auxiliary substances and additives which are usual or conventional for materials of this kind. Examples in that respect are fillers, thickening agents or viscosity regulators, moisture-retaining agents, vitamins, plant extracts, emulsifiers, dissolving aids, dispersing aids, perfumes, aroma substances, anti-oxidants and preserving agents which can be used in the usual levels of concentration. Preferably the gel material according to the invention is water-free so that preserving agents are not absolutely necessary as under those conditions micro-organisms cannot find suitable living conditions. The use of anti-oxidants is to be recommended however, In particular when the oil component contains constituents with unsaturated fatty acids in order to prevent the gel material according to the invention from becoming rancid or spoiling. It is also to be noted in this respect that certain metal oxides, that is to say pigments, can have a catalytic effect on the material becoming rancid.

The total amount of auxiliary substances and additives should not exceed 50% by weight and preferably together with the amount of pigments should be in a range of between 0.1 and 50% by weight, preferably between 1 and 45% by weight and particularly preferably in a range of between 5 and 35% by weight.

The pigmented oil-based gel material according to the invention can be put into any forms. Particularly preferably, it is shaped into the form of leads and used in the form of pencils. A further advantage of the oil material according to the invention is that it can be shaped with casting and extrusion processes. Particularly preferably the gel material according to the invention is processed to form color pencils and cosmetic pencils. The leads produced, having a gel structure, enjoy the advantage that they can be applied in the form of slender, independent leads, and equally well in the form of leads which are 'encased'—that is to say accommodated in wood or plastic material—without deforming or indeed breaking off or smearing.

A further subject of the invention is a color pencil which includes a sharpenable sheath of wood or a wood substitute or plastic material with, embedded therein, a lead comprising a pigmented oil-based gel material. Preferably the color pencil is a cosmetic pencil and particularly preferably it is a lipstick, eyeshadow pencil, lipliner pencil, eyeliner pencil, kohl pencil, kajal pencil or eyebrow pencil or a covering pencil, referred to as a 'concealer'.

The color pencil according to the invention is produced by a procedure whereby the pigmented gel material produced in accordance with the invention is heated above its melting point and poured in the liquid condition into a sheath blank, or the pigmented gel material is extruded and the molding obtained in that way, a portion of an endless extrusion, is laid into grooved board portions of wood, a wood substitute or plastic material, glued to a further grooved board portion to form blanks for about 10 pencils in each case and then subjected to further processing to provide finished pencils, using the processes which are usual in relation to lead pencils. In a further casting process the gel material according to the invention which is heated above its melting point is cast in molds and after cooling removed from the mold and used in suitable application units. It is also possible for those application units to be fitted with a lead-holding portion on to a mold and for the gel material according to the invention which has been heated above its melting point to be poured in through the lead-holding portion and, after cooling, the finished lead which is then disposed fixedly in the lead-holding portion can be turned back into the application unit. That process is particularly suitable for the rational production of cosmetic pencils in large numbers.

With this manner of manufacture, the advantageous properties of the gel material according to the invention in respect of tensile strength, flexural strength and resistance to fracture are particularly relevant.

The leads produced from the pigment-bearing gel material according to the invention on a lipid basis have very positive properties by virtue of the improved oil-binding capability thereof and improved temperature stability. For example they can still be used at up to about 45° C. The color leads then still have sufficient hardness and stability and can be well sharpened—the casings of those color leads can therefore easily be subjected to cutting machining in per se known manner.

A further subject of the invention is a process for the production of pencils using the gel material according to the invention as is defined in claims 27 and 30.

By virtue of the stability of the gel material it can be processed without any problems to form leads, even very thin leads, with a very disadvantageous ratio of length to diameter, for example the gel material can be heated above its melting point and then shaped. What is essential in that respect is that the material when heated above its melting point has only a low level of viscosity and can therefore be well worked in casting processes. As on the one hand the gel material is highly homogeneous and temperature-stable and on the other hand the shaped leads have adequate strength, the pencils can be produced by a procedure whereby the gel material according to the invention is poured directly into sheath blanks or the lead-guide portions of an application unit or into casting molds on to which a rotary mechanism has been fitted. In that case the gel material is cast through a lead-holding portion which is shaped for that purpose, within the rotary mechanism. It is however also possible in a separate first working step firstly to produce leads by casting or extrusion, and then to fit them into the desired sheath or rotary mechanism, or to process them to form pencils in a known casing, using the methods which are known in relation to lead pencil technology. Those alternative configurations afford advantages, and the most appropriate embodiment can be selected for the respective purpose involved.

In accordance with an embodiment to produce leads the pigmented gel material is shaped by casting or extrusion. A preferred procedure is shaping with casting processes using the gel material according to the invention which has been heated above the melting point, as in that case the material can be poured directly into the sheath blank comprising a sharpenable material, which is provided for receiving the lead. The blank is then subjected to further processing using per se known processes to form a pencil with the lead. That can minimise rejection wastage.

In another preferred embodiment the gel material according to the invention which has been heated above the melting point is poured into the lead-guide portion of an application unit, preferably of a rotary mechanism, and, after cooling, connected to the remaining components of the application unit to form a finished rotary mechanism.

In a further preferred embodiment the pigmented gel material according to the invention is used to shape a lead by casting or extrusion and the lead is then fitted into a suitable rotary mechanism. The gel material according to the invention, even without support, is of such a stable structure that the lead disposed in a rotary mechanism can be extended from it or retracted into it by rotation without breaking off. It is therefore also highly suitable for the production of rotary pencils.

It will be self-evident in this respect that suitable measures must be taken for securely sealing off the application units or rotary mechanisms used if the pigmented gel material according to the invention on a lipid basis contains volatile components such as volatile silicone oils or isoparaffins. If the leads produced in accordance with the above-described processes are subjected to further processing using the processes known from the production of lead pencils, then the grooved board portions of wood or wood substitutes, which are used in that case, must obviously previously be sealed off in a suitable known manner to prevent the volatile components from diffusing thereinto.

The invention is described in greater by means of the examples hereinafter without being restricted thereto. The INCI designations which are known to the man skilled in the art have been used to identify the raw materials involved. The quantitative details are always given in percent by weight (% wt) with respect to the total weight of the finished preparation.

EXAMPLE 1

Eyeliner

|  | % wt |
|---|---|
| (1) Isostearyl alcohol | 6.500 |
| (2) C20–40 alkyl stearate | 12.000 |
| (3) Paraffin | 5.000 |
| (4) Buxus chinensis | 2.500 |
| (5) Ethylcellulose | 2.000 |
| (6) C1–5 alkyl galactomannan | 1.200 |
| (7) Pigments | 20.000 |
| (8) Behenamidopropyl dimethylamine behenate | 4.750 |
| (9) Ascorbyl palmitate | 0.100 |
| (10) Tocopherol | 0.100 |
| (11) Cyclomethicone | 45.850 |

For the production procedure the components (1) through (4) are put together and heated to about 85° C. until a fluid phase has occurred. The components (5) and (6) are dissolved therein and then component (7)—pigments—is added with agitation. The mixture is kept in the fluid condition with heating, then component (8) is added and dissolved in the mixture with agitation. Now about 40% of component (11) is added with agitation and the mixture is homogenised in a suitable manner to destroy the pigment agglomerates, for example by means of a three-roller mill, an Ultra-TURRAX, heated ball mill or the like. The mixture is then heated above the melting point again, in which case the components (9) and (10) and the remainder of component (11) are added and the overall mixture is thoroughly mixed. The finished mixture is then poured at about 80° C. into suitable molds and, after cooling, removed from the molds and subjected to further processing. That gives color leads for eyeliner pencils, with good color strength, with very pleasant application, which are highly transfer-resistant and which cannot be transferred on to other materials and which do not migrate from the location at which they are applied.

EXAMPLE 2

Lipliner

|  | % wt |
|---|---|
| (1) Isostearyl alcohol | 5.500 |
| (2) C20–40 alkyl stearate | 11.000 |
| (3) Paraffin | 2.000 |
| (4) Buxus chinensis | 2.500 |
| (5) Ethylcellulose | 1.500 |
| (6) C1–5 alkyl galactomannan | 1.200 |
| (7) Pigments | 35.000 |
| (8) Behenamidopropyl dimethylamine behenate | 4.750 |
| (9) Ascorbyl palmitate | 0.100 |
| (10) Tocopherol | 0.100 |
| (11) Cyclomethicone | 36.350 |

Production is effected in a similar manner to Example 1 but after addition of the remaining amount of component (11) the mixture is allowed to cool in a closed container and extruded in known manner to form leads. They are glued into grooved board portions, which are coated on the inside, consisting of wood, a wood substitute or plastic material, and processed in known manner to form color pencils.

Four comparative examples were conducted, in which the above-mentioned combination of oil-soluble ethylcellulose, C1–5 alkylgalactomannan and behenamidopropyl dimethylamine behenate was varied in such a way that in each case only two of those components were used to produce an eyeshadow pencil in accordance with Example 1. Production was effected similarly to Example 1:

COMPARATIVE EXAMPLES

Eyeliner

|  |  | (3) % wt | (4) % wt | (5) % wt | (6) % wt |
|---|---|---|---|---|---|
| (1) | Isostearyl alcohol | 6.500 | 6.500 | 6.500 | 6.500 |
| (2) | C20–40 alkyl stearate | 12.000 | 12.000 | 12.000 | 12.000 |
| (3) | Paraffin | 2.000 | 2.000 | 2.000 | 2.000 |
| (4) | Buxus chinensis | 2.500 | 2.500 | 2.500 | 2.500 |
| (5) | Ethylcellulose | 2.000 | — | 2.000 | 2.300 |
| (6) | C1–5 alkyl galactomannan | — | 1.200 | 1.200 | 2.200 |
| (7) | Pigments | 20.000 | 20.000 | 20.000 | 20.000 |
| (8) | Behenamidopropyl dimethylamine behenate | 4.750 | 4.750 | — | — |
| (9) | Ascorbyl palmitate | 0.100 | 0.100 | 0.100 | 0.100 |
| (10) | Tocopherol | 0.100 | 0.100 | 0.100 | 0.100 |
| (11) | Cyclomethicone | 50.050 | 50.850 | 55.600 | 54.300 |

Comparative Example 3

The material acts generally non-homogeneously and forms layer-like structures. The leads are hard, they deliver irregularly and they break very easily. The material when heated above the melting point is highly viscous and difficult to pour, and the viscosity is retained even when there is a further increase in temperature. In a processing procedure in accordance with Example 2, upon extrusion of the material, the result obtained is brittle leads which break very easily.

Comparative Example 4

The material sets to form very soft leads which can be removed from the mold only with a very great deal of difficulty. The lead material remains pasty in its interior. The color leads can already no longer be used at room temperature. In a processing procedure in accordance with Example 2 the cooled material cannot be extruded as it flows in the form of a soft paste out of the extruder. No color leads which have acceptable properties of use can be produced in that way.

Comparative Example 5

The material is highly viscous and difficult to pour. The leads are very firm and provide poor and irregular delivery of color. Severe separation of cyclomethicone occurs at the surface of the color lead. In a production procedure in accordance with Example 2, it is not possible to obtain usable color leads by extrusion as the majority of color leads break a number of times or even totally crumble away.

Comparative Example 6

The material is highly viscous and can no longer be processed by pouring. An increase in temperature to 120° C. does not result in a reduction in viscosity. A processing procedure in accordance with Example 2 does not give usable color leads, by extrusion. Leads produced in that way are hard, they break very easily and they exhibit poor irregular delivery of color. Severe separation of cyclomethicone on the surface of those color leads occurs.

The invention claimed is:

1. A pigment-bearing gel material based on lipids, comprising:
    (a) between 0.1 and 20% by weight of oil-soluble alkylcellulose having alkyl residues selected from the group consisting of straight-chain and branched and having between 1 and 10 carbon atoms,
    (b) between 0.1 and 20% by weight of alkylgalactomannan polysaccharide having an alkyl residue between 1 and 10 carbon atoms, and
    (c) between 0.1 and 30% by weight of a salt from a long-chain fatty acid having between 16 and 24 carbon atoms and a fatty acid amidoalkyldialkylamine.

2. A gel material as set forth in claim 1, wherein the oil-soluble alkylcellulose is oil-soluble ethylcellulose.

3. A gel material as set forth in claim 1, wherein the alkygalactomannan polysaccharide is C1–5 alkylgalactomannan.

4. A gel material as set forth in claim 1, wherein the salt from a long-chain fatty acid and a fatty acid alkylamidodialkylamine is selected from the group consisting of stearylamidopropyl dimethyl lamine stearate, behenamidopropyl dimethylamine stearate, stearoylamidopropyl dimethylamine behenate, behenamidopropyl dimethylamine behenate and mixtures thereof.

5. A gel material as set forth in claim 1, wherein the salt is a behenamidopropyl dimethylamine behenate.

6. A gel material as set forth in claim 1, comprising:
    (a) between 0.1 and 20% by weight of oil-soluble ethylcellulose,
    (b) between 0.1 and 20% by weight of C1–5 alkylgalactomannan, and
    (c) between 0.1 and 30% by weight behenamidopropyl dimethylamine behenate.

7. A gel material as set forth in claim 1, comprising:
(a) between 0.25 and 10% by weight of oil-soluble ethylcellulose,
(b) between 0.25 and 10% by weight of C1–5 alkylgalactomannan, and
(c) between 0.30 and 20% by weight behenamidopropyl dimethylamine behenate.

8. A gel material as set forth in claim 1, comprising:
(a) between 0.4 and 4% by weight of oil-soluble ethylcellulose,
(b) between 0.4 and 4% by weight of C1–5 alkylgalactomannan, and
(c) between 0.5 and 6% by weight behenamidopropyl dimethylamine behenate.

9. A gel material as set forth in any one of claims 1 through 8, wherein the oil-soluble ethylcellulose and the C1–5 alkylgalactomannan are used in a ratio of between 0.3:1 and 3:1 relative to each other.

10. A gel material as set forth in one of claims 1 through 8, wherein behenamidopropyl dimethylamine behenate is in a ratio of between 0.5:1 and 5:1 to the total amount of the other two constituents of the combination.

11. A gel material as set forth in one of claims 1 through 8, further comprising an oil component wherein the oil component is selected from the group consisting of vegetable, animal, mineral synthetic oil, fat, non-volatile silicon oil, volatile silicone oil, wax and mixtures thereof.

12. A gel material as set forth in claim 11, wherein the oil component is present in an amount of between 1 and 70% by weight with respect to the total weight of the composition.

13. A gel material as set forth in claim 12, wherein the oil component is selected from the group consisting of castor oil, sunflower oil, sesame seed oil, rapeseed oil, hydrated coconut oil, hydrated palm oil, jojoba oil, mineral oil, paraffin, petroleum jelly, lanolin, lanolin derivatives, volatile isoparaffin, cyclomethicone, dimethicone, phenyltrimethicone and mixtures thereof.

14. A gel material as set forth in claim 11, wherein wax is present between 0.1 and 30% by weight with respect to the total weight of the composition.

15. A gel material as set forth in claim 14, wherein the wax contains one of a natural, mineral and synthetic wax.

16. A gel material as set forth in claim 14, wherein the wax is selected from the group consisting of beeswax, modified beeswax, carnauba wax, candelilla wax, Japan wax, ouricuri wax, flower wax, orange flower wax, jasmine wax, fruit wax, apple wax, orange wax, lignite wax, microcrystalline wax, long-chain fatty alcohols, esters of long-chain fatty alcohols and long-chain fatty acids and mixtures thereof.

17. A gel material as set forth in claim 16, wherein the long-chain fatty alcohol is selected from the group consisting of cetylalcohol, stearylalcohol, behenylalcohol and mixtures thereof.

18. A gel material as set forth in claim 16, wherein the ester of long-chain fatty alcohol and long-chain fatty acid is selected from the group consisting of cetylpalmitate, cetearylpalmitate, stearylstearate, behenylstearate, C20–40 alkylstearate and mixtures thereof.

19. A gel material as set forth in claim 11, further comprising auxiliary substances and additives in a proportion of between 0.1 and 50% by weight with respect to the total weight of the composition.

20. A gel material as set forth in claim 11, further comprising pigments in an amount of between 0.1 and 50% by weight with respect to the total weight of the composition.

21. A gel material as set forth in claim 11, further comprising pigments in an amount of between 1 and 45% by weight with respect to the total weight of the composition.

22. A gel material as set forth in claim 11, further comprising pigments in an amount of between 5 and 35% by weight with respect to the total weight of the composition.

23. A gel material as set forth in claim 21, wherein the pigments are selected from the group consisting of titanium dioxide, iron oxides, ultramarine blue, chromium oxide green, chromium hydroxide green, Berlin Blue, mica, sheen pigments, flake-form metal powders, finely divided PET flakes, flakes of organic coloring agents and mixtures thereof.

24. A gel material as set forth in claim 1, wherein the material is in the form of one of a cast and extruded lead.

25. A color pencil including a lead comprising a gel material as set forth in claim 11, wherein the lead is surrounded by one of a sheath blank of wood, a wood substitute and plastic material.

26. A color pencil including a lead comprising a gel material as set forth in claim 23, wherein the lead is fixed in a rotary mechanism of a rotary pencil.

27. A color pencil as set forth in claim 26, wherein the pencil is a cosmetic pencil.

28. A color pencil as set forth in claim 27, wherein the cosmetic pencil is selected from the group consisting of lipstick, lipliner pencil, eyeshadow pencil, eyeliner pencil, kohl pencil, kajal pencil, eyebrow pencil and concealing pencil.

29. A process for the production of the color pencil of claim 26 comprising the steps of melting and casting the gel material into a sheath blank to form the pencil.

30. A process for the production of the color pencil of claim 26, including extruding the gel material to form a blank, cutting the blank length to form portions leads.

31. A process for the production of a color pencil as set forth in claim 26, wherein the gel is melted and poured through a lead-holding portion, which is fitted on to a casting mold, of a rotary mechanism, and the lead formed after cooling, after removal from the mold, is rotated into the rotary mechanism of a rotary pencil.

32. A process for the production of a color pencil as set forth claim 26, wherein the gel is melted and poured into a casting mold and the lead formed after cooling, is fitted into the lead-holding portion of a rotary mechanism of a rotary pencil.

* * * * *

UNITED STATES PATENT AND TRADEMARK OFFICE
CERTIFICATE OF CORRECTION

| | | |
|---|---|---|
| PATENT NO. | : 7,150,784 B2 | Page 1 of 1 |
| APPLICATION NO. | : 10/500527 | |
| DATED | : December 19, 2006 | |
| INVENTOR(S) | : Christian Sproger et al. | |

It is certified that error appears in the above-identified patent and that said Letters Patent is hereby corrected as shown below:

Col. 11, Line 19
Claim 10, line 1, --any-- should be inserted after "in".

Signed and Sealed this

Twelfth Day of June, 2007

JON W. DUDAS
*Director of the United States Patent and Trademark Office*